April 18, 1972 R. L. BYRUM Plant Pat. 3,126
ROSE PLANT
Filed June 1, 1970
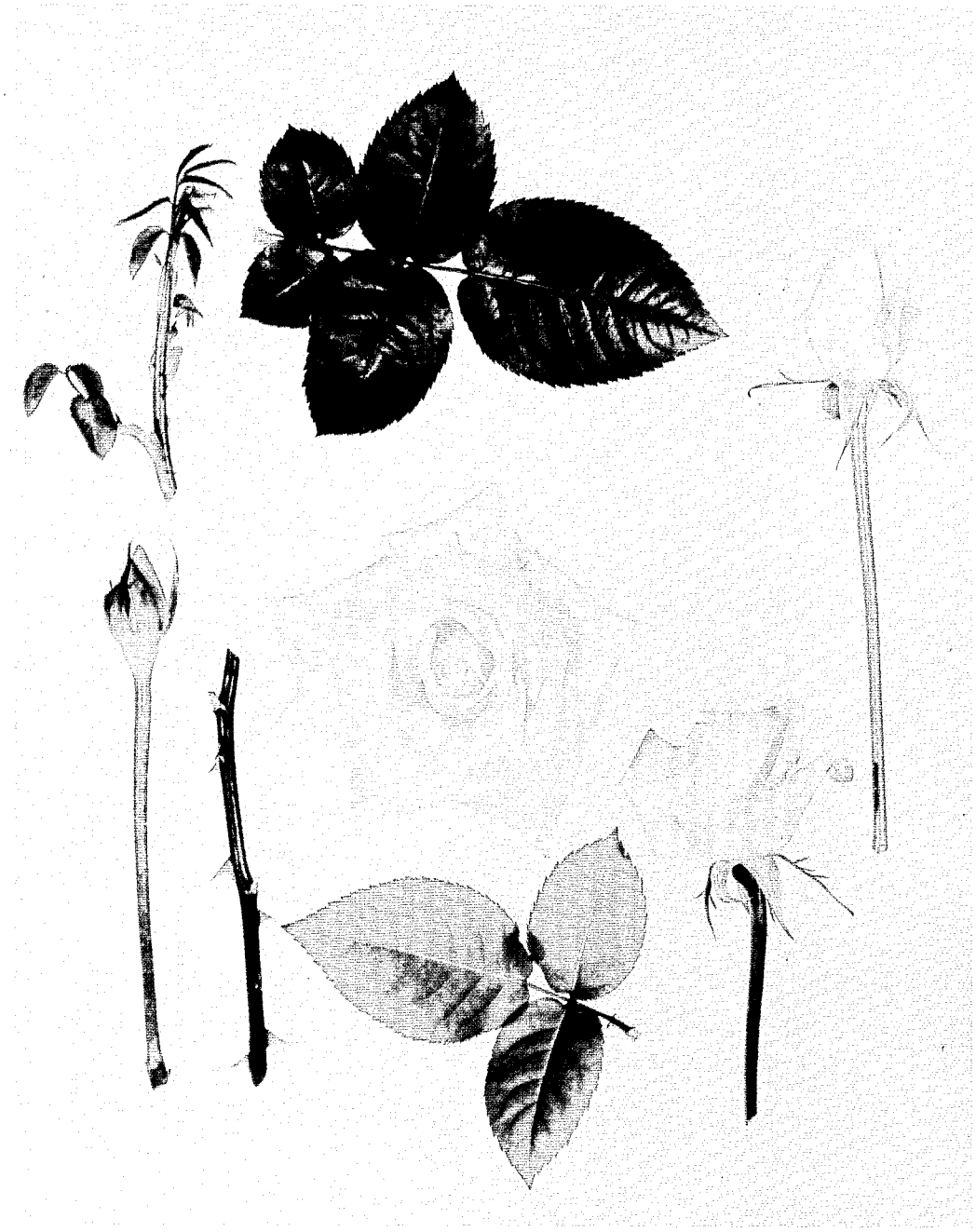
INVENTOR.
ROY L. BYRUM
BY Rummler & Snow
Attys

United States Patent Office

Plant Pat. 3,126
Patented Apr. 18, 1972

3,126
ROSE PLANT

Roy L. Byrum, Richmond, Ind., assignor to Joseph H. Hill Company, Richmond, Ind.

Filed June 1, 1970, Ser. No. 42,610
Int. Cl. A01h *5/00*
U.S. Cl. Plt.—18 1 Claim

ABSTRACT OF THE DISCLOSURE

A new variety of hybrid tea rose suitable for year around greenhouse forcing and distinguished by its continuous free production of large sized blooms having excellent petal texture, a pleasing coloration, extending from French Rose to Porcelain Rose, unusually strong and long stems, and a vigorous growth habit.

BACKGROUND OF THE INVENTION

This new variety of rose plant was produced by me by crossing Eternal Sun (P.P. 2,689), as the seed parent, with Carina (P.P. 2,378) with the object of developing a tea rose plant having the production and keeping qualities of Carina and the vigorous and strong growth habit of Eternal Sun for use as a greenhouse forcing variety that would not be adversely affected by lack of sunlight during the winter growing season. This plant resulted as a seedling from a crossing made by me in March 1966 at Richmond, Ind., and, upon its blooming in the spring of 1967, was observed to have much of the desirable characteristics I was seeking.

Asexual propagation of this new plant by rooting at Richmond, Ind., and by budding at Hamilton City, Calif., through succeeding generations at each place, has shown that all of the sought for characteristics for an improved greenhouse forcing variety of hybrid tea rose have been obtained and that these characteristics are fixed and hold true from generation to generation.

DESCRIPTION OF THE DRAWING

This new variety of rose plant is illustrated by the accompanying full color drawing showing the form of the opened flower and the buds and showing specimens of foliage and old and young wood.

DESCRIPTION OF THE PLANT

The following is a detailed description of my new variety of rose plant with specifications of color according to Koster's Color Guide, indicated by (K), and Robert S. Wilson Horticultural Chart, indicated by (W). All observations were made from plants and cut flowers grown in greenhouse in Richmond, Ind.

*The Plant*

Origin: Seedling (#67–3P).

Parentage:
- *Seed parent.*—Eternal Sun (P.P. 2689).
- *Pollen parent.*—Carina (P.P. 2378).

Classification: Hybrid tea rose.
Form: Bush.
Growth: Free and vigorous with large canes.
Habit: Upright and branched.
Main stems: Color—Spinach Green (W) 0960/3 blotched with Maroon (K) #97.
- *Thorns.*—Several, medium length, hooked downward and with long narrow base. Color—Base, Fawn (K) #89 changing to Tobacco Brown (K) #88 at tip.

- *Prickles.*—Few—Color—Tobacco Brown (K) #88.
- *Hairs.*—None.

Branches: Color—Spinach Green (W) 0960/1.
- *Thorns.*—Several, medium length, hooked downward, with long and narrow base. Color—Red Ochre (K) #94.
- *Prickles.*—Few. Color — Veronese Green (W) 660/3.
- *Hairs.*—None.

New shoots: Color—Spinel Red (W) 00823/2 to 00823/3.
- *Thorns.* — Several, medium length, downwardly hooked and with long narrow base. Color—Spinel Red (W) 0023/2 at base, gradually changing to 0023/3 at tip.
- *Prickles.*—Several. Color—Spinel Red (W) 0023.
- *Hairs.*—None.

Foliage: Quantity—abundant.
- *Leaves.*—Size—large and heavy. Shape—odd pinnate.
- *Leaflets.*—5 to 7 in number. Shape—ovid, with mucronate apex, round base, and simply serrate margins. Texture—leathery. Color—*mature*—upper surface, Spinach Green (W) 0960 under surface, Apple Green (K) plate #77. (Above are closest colors.) *Young*—upper surface, Spinel Red (W) 00823/2 to 00823/3; under surface, Spinel Red (W) 00823/2 to 00823/3.
- *Rachis.*—Heavy, with grooved upper side and prickly under side.
- *Stipules.*—Moderately long, wide with short points turned outward at an angle of less than 45° and recurved toward the stem.

*The bud*

Before calyx breaks:
- Size.—Medium large.
- Form.—Long pointed ovoid with a conspicuous neck, foliaceous appendages on the surface, and with stout bristle-like foliaceous parts extending beyond bud tip for a distance of ¼ or more of the bud length.
- *Color of calyx.*—Scheele's Green (W) 860/3 at the bottom, gradually changing toward Deep Carmine Violet (K) #46.

As calyx breaks: Color of bud.—Empire Rose (W) 0621/1 with edge bordered in (W) 0621.
As first petal opens:
- *Size (bud).*—Large.
- *Form.*—Long pointed ovoid.
- Color of petal.—Outside—Chartreuse (W) 663/1 at base, gradually changing to French Rose (W) 520 margined with Claret Rose (W) 021/1. Inside—Chartreuse Green (W) 663 at base, gradually changing to Azalea Pink (W) 618/2 overlaid with shades of Azalea Pink (W) 618/1.

Bud Opening: Opens up well at normal rate.
Sepals: Permanent, medium length, spear shaped, some curled. Color.—Inside—Scheele's Green (W) 860/2 overlaid with white fuzz. Outside—Scheele's Green (W) 860/1 with lighter streak of 860/2 through center of sepal. Peduncle: Erect, smooth, medium length, large diameter and very strong.
- *Color.*—Scheele's Green (W) 860.
- *Thorns.*—None. Hairs: None.
- *Prickles.*—Numerous. Color: Veronese Green (W) 660/3.

*The flower*

Blooming habit: Free. Continuous through all seasons.
Size: Very large. 4 to 5 inches in diameter fully opened.
Borne: Singly, on long, strong stems.
Shape: Full high centered, changing to open high centered as bloom matures. When first opening, petals are tightly rolled outward, becoming loosely rolled outward at maturity.
Petalage: Double with 35 to 40 regularly arranged petals. Shape: Obovate with obtuse apex. Inside petals have obtuse apex with one notch.

The following are observations of a greenhouse grown flower newly opened in September 1969 at Richmond, Ind.

*Color.*—Outside surface (all petals)—French Rose (W) 520/2 with Chartreuse Green (W) 663/2 at the base; inside surface—*Outside petal*—French Rose (W) 520/1 with Chartreuse Green (W) 663/1 at base.

*Intermediate petal*—French Rose (W) 520/2 with Chartreuse Green (W) 663/1 at base.

*Inner petal*—French Rose (W) 520 with Chartreuse Green (W) 663/1 at base.

Peristence: Petals hang on and dry.
Fragrance: Penetrating tea.
Lasting Quality: Cut flowers—5 to 6 days at living room temperature in November 1969.
General color:
Effect of open bloom: Newly opened and 3 day old flower—French Rose (W) 520/3.

The following observations were made of a rose opened for three days in a greenhouse in November 1969 at Richmond, Ind.:

*Color of petals.—Outside and intermediate petals.*—outside surface—Porcelain Rose (W) 620/3; inside surface—Porcelain Rose (W) 620/3 with base of Chartreuse Green (W) 663/3. *Inner petals.*—outside surface—French Rose (W) 520/3; inside surface—French Rose (W) 520/2 with base of Chartreuse Green (W) 663/3.

*Reproductive organs*

Stamens: Many, regularly arranged about pistils.

*Anthers.*—Medium large—all open at once. Color—Apricot (W) 609/2.

*Filaments.*—Medium length, most with anthers. Color—Crimson (W) 22/2.

Pollen: Abundant. Color—Naples Yellow (W) 403/2.
Pistils: Many.
Styles: Uneven, medium length, bunched and moderately thin. Color—Camellia Rose (W) 622.
Stigmas: Color—Creamy White (K) #2.
Ovaries: Some protruding from calyx.

My new variety of tea rose is considered to be better than its seed parent because it has a larger bloom and much better keeping qualities. Likewise the new variety is an improvement over its pollen parent because it has a more pleasing color, stronger stems, and is not adversely affected by the lack of light during winter months. All in all, my new variety of tea rose is considered to be a superior greenhouse forcing variety.

I claim:

1. A new and distinct variety of rose plant substantially as herein shown and described, characterized by its pleasing French Rose to Porcelain Rose range of coloration, its free and continuous production of very large blooms with unusually strong stems, and its good growth and production for year around greenhouse forcing.

No references cited.

ROBERT E. BAGWILL, Primary Examiner